United States Patent [19]

Mozsary et al.

[11] 4,416,629

[45] Nov. 22, 1983

[54] OSSEOINTERFACED IMPLANTED ARTIFICIAL TOOTH

[76] Inventors: Peter G. Mozsary, 530 Tennessee Ave., Vallejo, Calif. 94590; Robert E. Lapcevic, 40 N. Gate Victoria Ave., Milpitas, Calif. 95035

[21] Appl. No.: 395,139

[22] Filed: Jul. 6, 1982

[51] Int. Cl.³ ............................................. A61C 8/00
[52] U.S. Cl. ..................................... 433/174; 433/173
[58] Field of Search ............... 433/173, 174, 175, 176, 433/169, 170, 220, 221, 201

[56] References Cited

U.S. PATENT DOCUMENTS

| | | | |
|---|---|---|---|
| 2,857,670 | 10/1958 | Kiernan, Jr. | 433/173 |
| 2,880,508 | 4/1959 | Lester et al. | 433/205 |
| 3,579,831 | 5/1971 | Stevens | 433/174 |
| 3,589,011 | 6/1971 | Sneer | 433/174 |
| 3,726,011 | 4/1973 | Savignano | 433/174 |
| 3,797,113 | 3/1974 | Brainin | 433/201 |
| 3,952,414 | 4/1976 | Shovers et al. | 433/173 |
| 3,955,280 | 5/1976 | Sneer | 433/174 |
| 3,979,828 | 9/1976 | Taylor | 433/173 |
| 4,086,701 | 5/1978 | Kawahara et al. | 433/174 |
| 4,178,686 | 12/1979 | Riess et al. | 433/201 |
| 4,195,409 | 4/1980 | Child | 433/175 |
| 4,215,986 | 5/1980 | Riess | 433/173 |
| 4,259,072 | 3/1981 | Hirabayashi et al. | 433/173 |
| 4,270,905 | 6/1981 | Mohammed | 433/173 |
| 4,318,696 | 3/1982 | Kasama et al. | 433/173 |
| 4,324,550 | 4/1982 | Reuther et al. | 433/174 |

FOREIGN PATENT DOCUMENTS

| | | | |
|---|---|---|---|
| 1075791 | 2/1960 | Fed. Rep. of Germany | 433/174 |
| 2401323 | 7/1974 | Fed. Rep. of Germany | 433/174 |
| 2413883 | 9/1975 | Fed. Rep. of Germany | 433/173 |

Primary Examiner—John J. Wilson
Attorney, Agent, or Firm—Theodore J. Bielen, Jr.

[57] ABSTRACT

An artificial tooth implantable in a jaw bone utilizing a tooth root having distal and proximal end portions. The distal end portion of the root extends into the jaw bone and is fixed to the jaw bone. A hollow root extends from the proximal end portion of the root which is accessible from the outer surface of the jaw bone, toward the distal end portion of the root. A post has a first end portion which extends into the hollow of the root and is fixed to the root. A second portion of the post extends outwardly from the hollow and has an outer surface which slopes downwardly toward the first portion of the post. A crown is connected to the second portion of the post.

8 Claims, 6 Drawing Figures

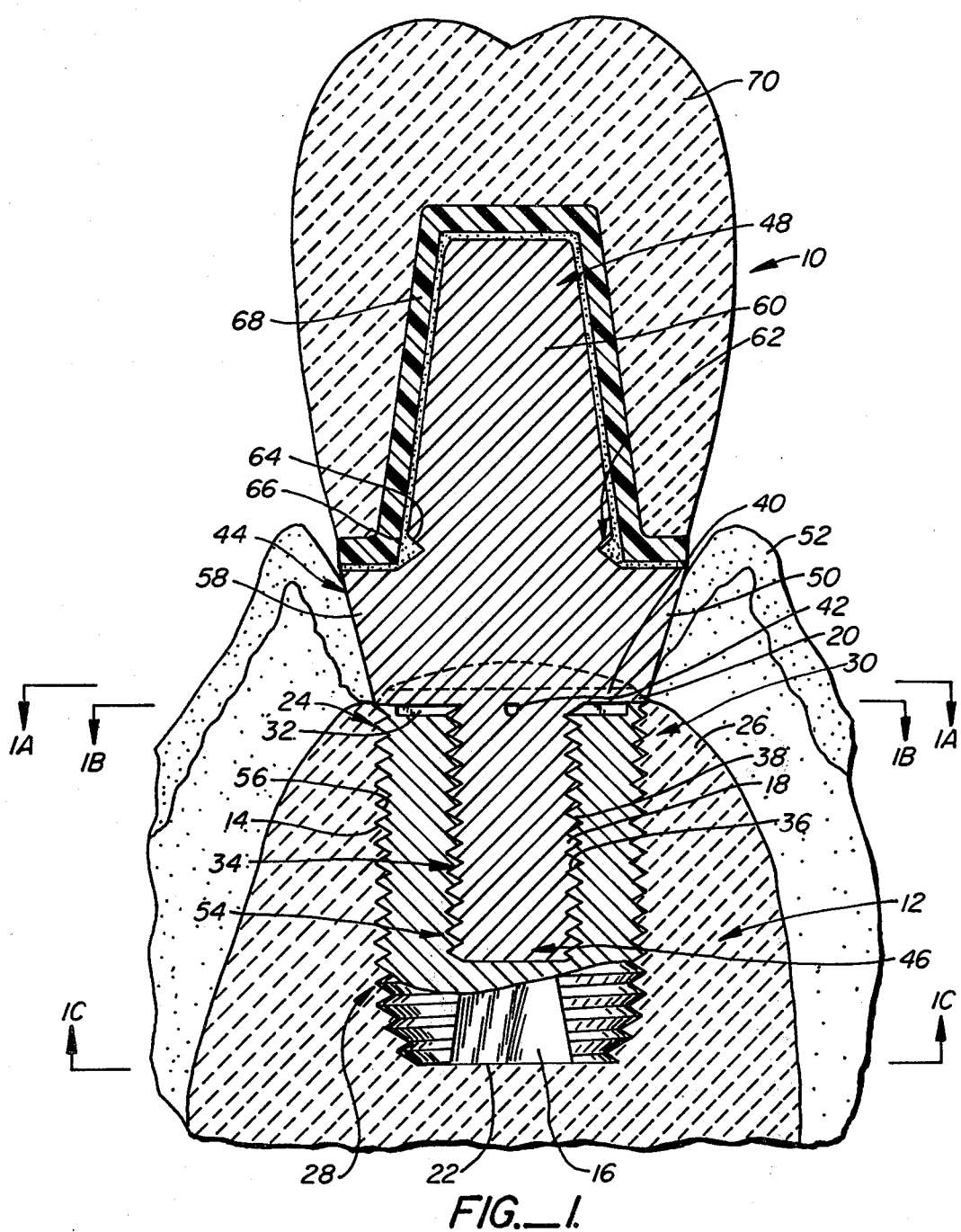
FIG._1.
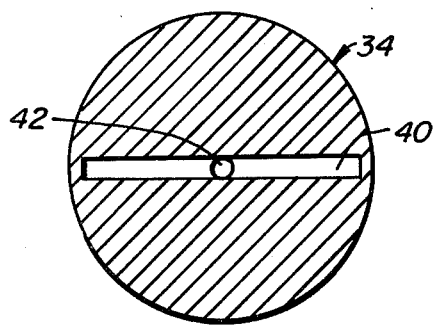
FIG._1A.
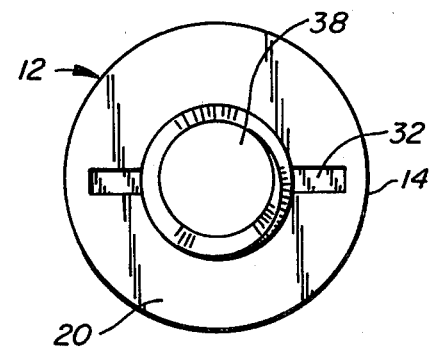
FIG._1B.

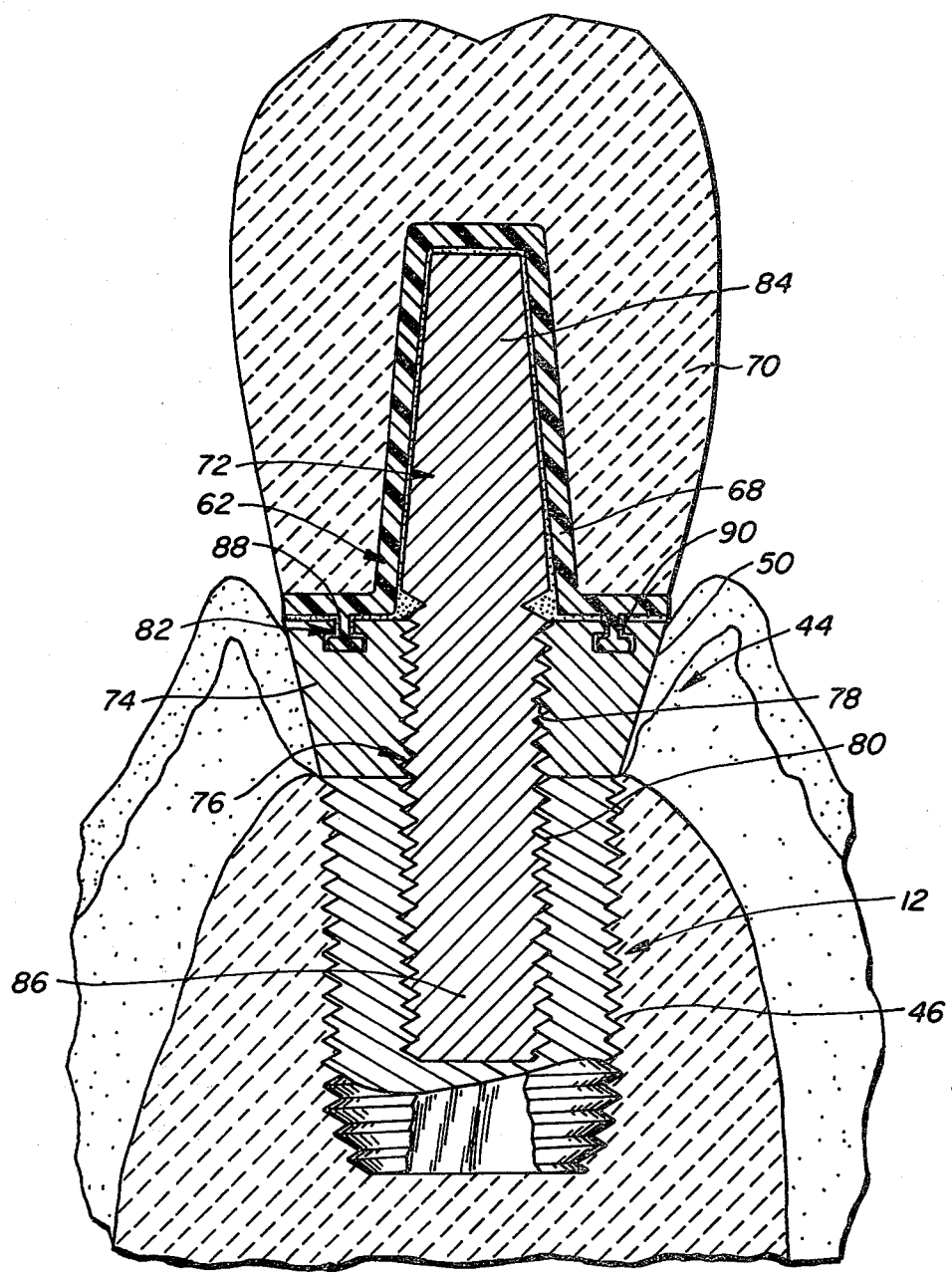
FIG._2.
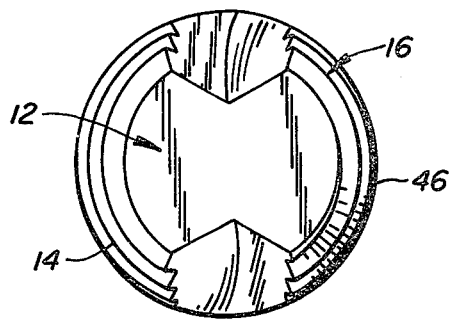
FIG._1C.

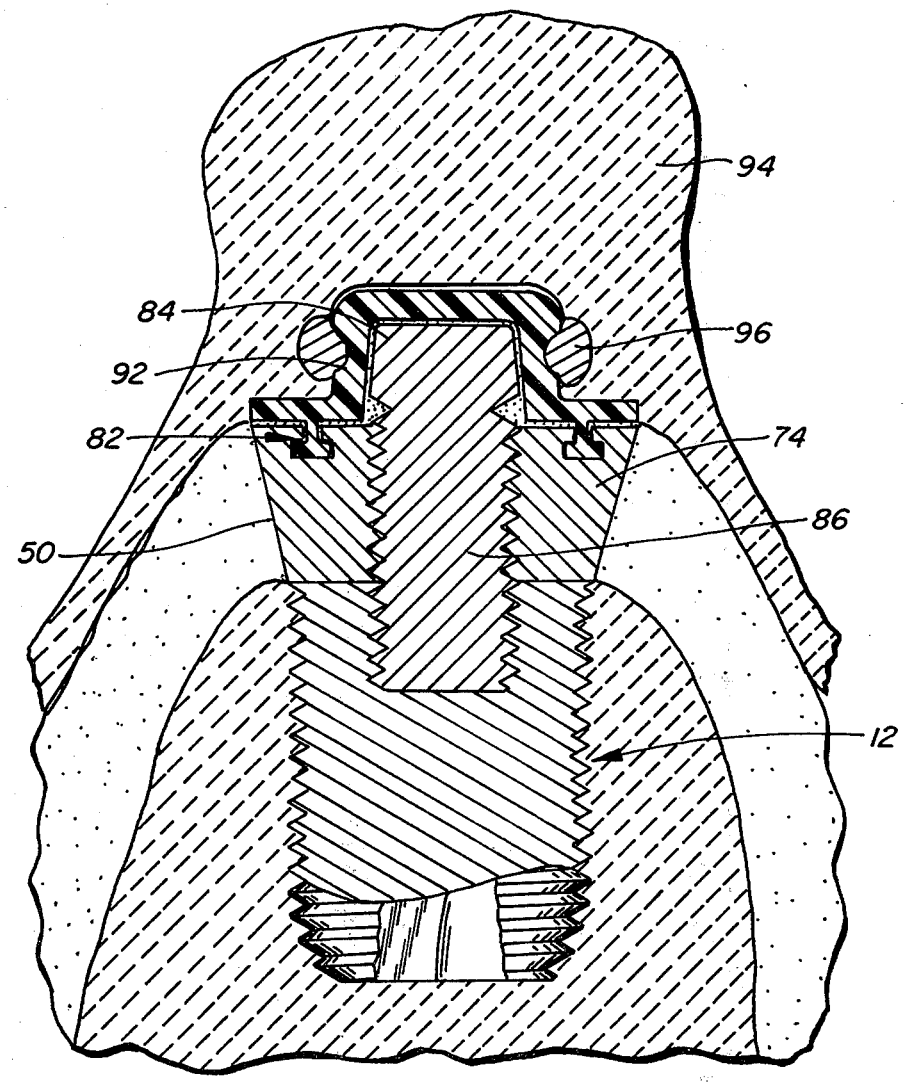
FIG._3.

OSSEOINTERFACED IMPLANTED ARTIFICIAL TOOTH

BACKGROUND OF THE INVENTION

The present invention relates to a novel osseointerfaced implanted artificial tooth which provides a permanent replacement for a natural tooth. In the past, many systems have been proposed for the implantation of artificial teeth. For example, diverse designs with screws, nails, blades, and the like which are loaded immediately upon insertion in the jaw bone. These implants generally result in scar formation around the implant with insufficient gingival seal, causing chronic infection, bone loss, and the eventual removal of the implant itself. For example, U.S. Pat. Nos. 2,857,670 and 3,579,831 describe these systems.

Later designs, such as that shown by U.S. Pat. No. 3,589,011, describe a two stage implant where a shank, or hollow pin, is used as the root of the artificial tooth. A superstructure is then attached to the shank by utilizing the hollow herewithin to support the super structure, including the crown of the artificial tooth thereabove. U.S. Pat. Nos. 3,797,113; 3,979,828; 4,178,686; 4,195,409; 4,259,072; 4,270,905; and 4,324,550 describe this type of system. The root portion in many cases becomes resorbable which eventually weakens the implant necessitating removal. Many materials such as polymethylmethacrylate eventually cause tissue necrosis and scar formation.

U.S. Pat. Nos. 4,215,986 and 4,318,696 describe implants which address the problem of protecting destruction of the artificial tooth by the masticatory forces that overload. It has been found that adjacent natural teeth have also been damaged by this type of implant, causing the breakdown of tissue supporting the natural tooth. An artificial implant system which overcomes the disadvantages of the prior art hereinabove described would be an extremely useful advance in the dental field.

SUMMARY OF THE INVENTION

In accordance with the present invention, a novel and useful osseointerfaced implant system is described which may be permanently affixed to the jaw bone is provided.

An artificial tooth of the present invention is implantable in the jaw bone (alveolar) and employs an implantable tooth root. The tooth root has a distal end portion extending into the jaw bone and a proximal end portion being accessible from the outer surface of the jaw bone. The root further includes a hollow extending from the proximal end portion of the root toward the distal end portion of the root. The root may include means for tapping, or self tapping the same in relation to the jaw bone during placement. Means is also provided for fixing the root to the jaw bone, such as a threaded surface. The hollow of the tooth root provides a place of fixation for the remainder of the artificial tooth. A post threads or otherwise fixes to the hollow of the tooth root and extends upwardly away from the jaw bone. The hollow may be sealed during a healing period to further strengthen the tooth root, and to maintain an unobstructed place of fixation for the post. The post may have a first portion fitting within the hollow of the root and a second portion extending outwardly from the hollow. The post second portion may also embrace an outer surface which slopes downwardly toward the first portion of the post, and inwardly toward the center of the post. This so called obtuse angle provides a tight contact between the gingiva and the implant and protects this contact as well.

A crown is then connected to the post, specifically the second portion of the post extending outwardly from the hollow of the tooth root. The second portion of the post may also be formed such that a base connects to the first portion of the post and a stem extends from the base of the second portion of the post. Means may also be provided for breakably connecting the base to the stem of the second portion of the post. In this manner, excessive lateral forces would shear the post rather than traumatizing the implant or the jaw bone itself.

To limit the elasticity of the upper structure, the second portion of the post may be coated with a polymer which would lie between the crown and the post. The polymer acts as a shock absorber and protects the bone against sudden high stress. Moreover, the polymer, or plastic coating, must have an elasticity which would limit mobility of the implant system; thus precluding damage to the bone around the natural teeth.

The base of the second portion of the post may include a dimension that extends a greater distance transversely in relation to the root than a transverse dimension of the stem of the second portion of the post. Thus a platform is provided for the plastic or polymer coating against shear stresses thereupon.

Another embodiment of the present invention utilizes a spacer and spline as the post. Means for fixing the spacer adjacent to spline and between the root and crown is also provided. The spacer may include the sloping outer surface of the post. Such a spacer would provide the dental practitioner with a method for adjusting the height of the same above the artificial tooth root. The spacer would also have means of turning the same in relation to the spline. Thus, the spacer and post fittingly engage one another.

The implant of the present invention may also include means for permitting the attachment of a denture to the post and the plastic, metal or like coating there around.

It may be apparent that a novel and useful artificial tooth implantable in the jaw bone has been described. It is therefore an object of the present invention to provide an artificial tooth implantable in a jaw bone which provides satisfactory service over a long term.

It is another object of the present invention to provide an artificial tooth implantable in a jaw bone which closely resembles the mobility of the natural tooth, thus permitting the patient to chew in a normal manner and protect against parafunctional forces.

It is yet another object of the present invention to provide an artificial tooth implantable in a jaw bone which may be used in substitution for a single tooth or a group of teeth as well as being connectable to natural teeth.

Still another object of the present invention is to provide an artificial tooth implantable in a jaw bone which protects against food particles being wedged between the gingiva and the implant during the chewing process, and against traumatizing of the contact site between the gingiva and implant.

Yet another object of the present invention is to provide an artificial tooth implantable in a jaw bone which has a predetermined breakage point of a portion thereof, upon the application of a predetermined shear force, thus protecting the implant and/or the jaw bone itself.

Another object of the present invention is to provide an artificial tooth implantable in the jaw bone which utilizes a post having a removable section which permits the dental practitioner to adjust the height of the post in relation to the tooth root.

Another object of the present invention is to provide an artificial tooth implantable in the jaw which permits the dental practitioner to remove all portions of the implant, and replace the same with new portions, except the artificial root.

The invention possess other objects and advantages, especially as concerns particular characteristics and features thereof which will become apparent as the specification continues.

BRIEF DESCRIPTION OF THE DRAWINGS

FIG. 1 is a sectional view of an embodiment of the present invention showing a portion of the jaw and gum in broken away configuration.

FIG. 1A is a view taken along line 1A—1A of FIG. 1.

FIG. 1B is a view taken along line 1B—1B of FIG. 1.

FIG. 1C is a view taken along line 1C—1C of FIG. 1.

FIG. 2 is a sectional view of another embodiment of the present invention.

FIG. 3 is a sectional view of another embodiment of the present invention.

For a better understanding of the invention, reference is made to the following detailed description of the preferred embodiment which should be taken in conjunction with the hereinabove described drawings.

DESCRIPTION OF THE PREFERRED EMBODIMENTS

Various aspects of the present invention will evolve from the following detailed description which should be taken in conjunction with the hereinabove described drawing. The invention as a whole is shown in the figures by reference character 10 and may include as one of its elements an implantable tooth root 12.

Root 12 may be constructed of a relatively rigid biocompatable material. For example, titanium would be a satisfactory material under this criteria. Root 12 is roughly cylindrical in shape and possesses a threaded surface 14. Root 12 may also include a self tapping construction, FIG. 1 broken away portion, of known construction. Root 12 includes a hollow portion 18 which extends from the upper surface 20 of root 12 toward the lower surface 22 thereof. Thus, proximal end portion 24 of root 12 extends to the outer surface of jaw bone 26. Distal end portion 28 of root 12 extends into the jaw bone 26 as far as is necessary for a satisfactory implantation. Threaded surface 14 of root 12 threadingly engages the threaded surface of jaw bone, FIG. 1C, 26 created by self tapping means 16. Thus, this threading engagement may be considered means 30 for fixing root 12 to jaw bone 26. Slot 32 permits the user to use a driving means to turn root 12 during the tapping of jaw bone 26. It should be noted that a screw 34 is temporarily placed in hollow proportion 18 and is held in place by the threaded surface 36 of screw 34 engaging threaded surface 38 of root 12 within hollow portion 18. Turning to FIG. 1A, it may be seen that screw 34 is temporarily inserted into hollow 18 during first stage of the implant which will be further described hereinafter.

Post 44 includes a first portion 46 which fits within hollow 18 of root 12. A second portion 48 extends outwardly from hollow 18 and upwardly from the surface of jaw bone 26. Second portion 48 includes an outer surface 50 which slopes downwardly toward first portion 46 of post 44 and inwardly toward the center of post 44. This permits the tight fitting of gingiva 52 to the outer surface 50. The sloping surface 50 also acts as a shelter against food particles wedging between surface 50 and gingiva 52. It should be added that the prevention of food particles from entering the space between the gingiva and the outer surface 50 of the post prevents damage to the implant and the living tissue thereat. Means 54 fixes first portion 46 of post 44 within hollow 18 of root 12. Such means may take the form of providing first portion 46 of post 44 with a threaded surface 56 which engages threaded surface 38 of hollow 18. It may be apparent that threaded surface 36 of screw 34 previously engaged the same threaded surface 38 of hollow 18, FIG. 1B. Post 44 may again be constructed of a fairly rigid material such as titanium. Second portion 48 of post 44 may include a base 58 connected to first portion 46 of post 44. Stem 60 extends from base 58 upwardly from jaw bone 26. As shown in the embodiment in FIG. 1, stem 60 is narrower transversely than base 58. Means 62 breakably connects base 58 to stem 60. In other words, second portion 48 of post 44 includes a weakened undercut portion 64 which surrounds the connection area between base 58 and stem 60. Thus, any excess lateral or shear forces will cause the breakage of stem 60 in relation to base 58 and thereby protect root 12 in bone 26. Undercut portion 64 is filled with a glue 66 which also surrounds stem 60. Glue 66 is used to attach a layer of resilient material 68 such as silicone, polysulphone, and the like. The thickness in quality of resilient layer 68 may be predetermined to restrict the range of movement of the upper structure to about 200 microns. Resilient layer 68 also acts as a shock absorber to protect the bone 26 against sudden high stress. Finally, a crown 70 may be formed as shown in FIG. 1.

Turning to FIG. 2, it may be seen that another embodiment of the present invention is provided. Post 44 includes a first portion 46 which fixes to root 12 in the same manner as the post shown in FIG. 1. However, the upper portion 48 has been split into a spline 72 and a washer, or spacer 74. Means 76 fixes spacer 74 to spline 72. As shown in FIG. 2, means 76 takes the form of a threaded outer surface 78 of spline 72 engaging a threaded surface 80 of spacer 74. Means 82 is provided for turning spacer 74 in relation to spline 72. Upper portion 84 of spline 72 may again break in relation to lower portion 86 thereof via means 62. In certain cases, spacer 74 may be replaced with one having a different height to compensate for dimensional adjustments to root 12. Means 82 in the form of openings 88 and 90 permit the use of tool to perform this turning or rotational action.

Turning to FIG. 3, it may be seen that upper portion 84 of spline 72 may be reduced in size and a new resilient layer having a groove 92 is placed over upper portion 84. A denture 94 may be snapped into place by the use of "O" ring 96. It should be noted that if any portion of spline 72 or post 44 break by the use of means 62, remainder of post 44 or spline 72 within root 12 may be removed and replaced.

In operation the jaw bone 26 is made visible to the dental practitioner by the use of a surgical device. Root 12 is tapped into place using tapping means 16 such that upper surface 20 of root 12 is accessible at the outer surface of bone 26. The drills used to locate the root opening are cooled to protect the bone against burning during this process. Screw 34 is inserted into hollow 18 of root 12 and covered by gingiva 52 for approximately four months. After this time period pilot hole 42 permits the dental practitioner to locate screw 34 through the gingiva 52 covering screw 34. A special cutting instrument removes the overlying tissue to reveal screw 34. Screw 34 is then removed and post 44 or spline 72 and spacer 74 are inserted within hollow 18 of root 12. It should be apparent that the superstructure consisting of the crown and resilient layer 68 could be attached to post 44 or spline 72 and spacer 74 after fixation of the post 44 or spline and spacer 72 and 74 to root 12. Resilient layer 68 will separate under pressure, such as the pressure applied by a plier-like device. Separation of resilient layer 68 from post 44 permits the dental practitioner to inspect, and/or alter the superstructure of the implant system. Post 44 would also be removable from root 12. As heretofore described, spacer 74 may be replaced with a spacer of a different height. Upper portion 84 of spline 72 may be cut down to provide for the insertion of a denture. Thus, all portions of the artificial tooth are replaceable, except the root 12.

While on the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An artificial tooth implantable in a jaw bone comprising:
   a. an implantable tooth root, said root having a distal end portion intended for extending into the jaw bone and a proximal end portion being accessible from the outer surface of the jaw bone; said root further including a hollow extending from said proximal end portion of said root toward said distal end portion of said root;
   b. means for fixing said root to the jaw bone;
   c. a post, said post having a first portion fitting within said hollow of said root and a second portion extending outwardly from said hollow; said second portion having an outer surface which slopes downwardly toward said first portion of said post said second portion of said post further including a base connected to said first portion or said post; a stem extending from said base; and a weakened portion at said connection between said base and stem for breakably connecting said base to said stem;
   d. means for fixing said first portion of said post within said hollow of said root;
   e. a crown connected to post.

2. The artificial tooth of claim 1 in which said weakened portion at said connection between said base and stem for breakably connecting said base to said stem includes an undercut portion thereat.

3. The artificial tooth of claim 2 which further comprises a layer of resilient material laminated between said crown and said post.

4. The artificial tooth of claim 3 in which said second portion of said post, and said layer of resilient material further include means for holding a denture thereto.

5. The artificial tooth of claim 2 in which said base of said second portion of said post includes a dimension that extends a greater distance transversly in relation to said root than a transverse dimension of said stem of said second portion of said post, said second portion outer surface sloping downwardly toward said post being defined to also slope inwardly toward the center of said post.

6. The artificial tooth of claim 1 which said post additionally comprises a spacer and means for fixing said spacer adjacent said post between said root and said crown, said spacer providing said sloping outer surface.

7. The artificial tooth of claim 6 in which said spacer includes means for turning said spacer in relation to said post.

8. The artificial tooth of claim 7 in which said root includes means for tapping said root in relation to the jaw bone during placement of said root in the jaw bone.

* * * * *